US00PP18125P3

(12) United States Plant Patent
Lemon

(10) Patent No.: US PP18,125 P3
(45) Date of Patent: Oct. 16, 2007

(54) ***GERANIUM* PLANT NAMED 'PATRIOT ROSE PINK'**

(50) Latin Name: *Pelargonium×hortorum*
Varietal Denomination: Patriot Rose Pink

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 212 days.

(21) Appl. No.: 11/177,659

(22) Filed: Jul. 8, 2005

(65) Prior Publication Data

US 2007/0011792 P1 Jan. 11, 2007

(51) Int. Cl.
*A01H 5/00* (2006.01)

(52) U.S. Cl. ..... Plt./328

(58) Field of Classification Search ..... Plt./328
See application file for complete search history.

*Primary Examiner*—Kent Bell
(74) *Attorney, Agent, or Firm*—The Webb Law Firm

(57) ABSTRACT

'Patriot Rose Pink' is a new variety of *geranium* that exhibits free flowering, excellent outdoor performance, and vibrant hot pink flowers with white eyes atop of mounding medium green foliage.

1 Drawing Sheet

Botanical classification: *Pelargonium×hortorum.*
Varietal denomination: 'Patriot Rose Pink'.

BACKGROUND OF THE INVENTION

The present invention comprises a new and distinct cultivar of *Pelargonium×hortorum* known by the varietal name 'Patriot Rose Pink'. The new variety was discovered in Lompoc, Calif. The new variety is a result of cross breeding Pink Seedling #2491 (female parent) (unpatented) and 'Valentine' (male parent) (U.S. Plant Pat. No. 10,587). The purpose of the breeding program was to introduce a new zonal *geranium*. The new variety is similar in plant type and flower color to its female parent, but is more free flowering. The new variety is similar in earliness to its male parent, but has more of a rose pink petal color. 'Patriot Rose Pink' is similar in flower size and color to 'Rocky Mountain Deep Rose', but has a more compact habit. The excellent outdoor performance and free flowering nature of 'Patriot Rose Pink' distinguishes the new variety from other varieties known to the breeder. The new variety was first asexually reproduced by cuttings in Connellsville, Pa. The new variety has been trial and field tested and has been found to retain its distinctive characteristics and remain true to type through successive propagations.

The new variety was grown in a glass greenhouse in a 4" pot in Connellsville, Pa. using full light, 16° C. night temperature, 20° C. day temperature, and grown in a soilless media with constant fertilizer at 200–250 ppm nitrogen and potassium. The new variety exhibits developed roots at 21 days at an average temperature of 23° C. and has a response time of six to seven weeks from a rooted cutting to flowering in a 10 cm. container.

DESCRIPTION OF THE DRAWING

The accompanying photographic drawing illustrates the new variety, with the color being as nearly true as is possible with color illustrations of this type.

DESCRIPTION OF THE PLANT

Figure 1:
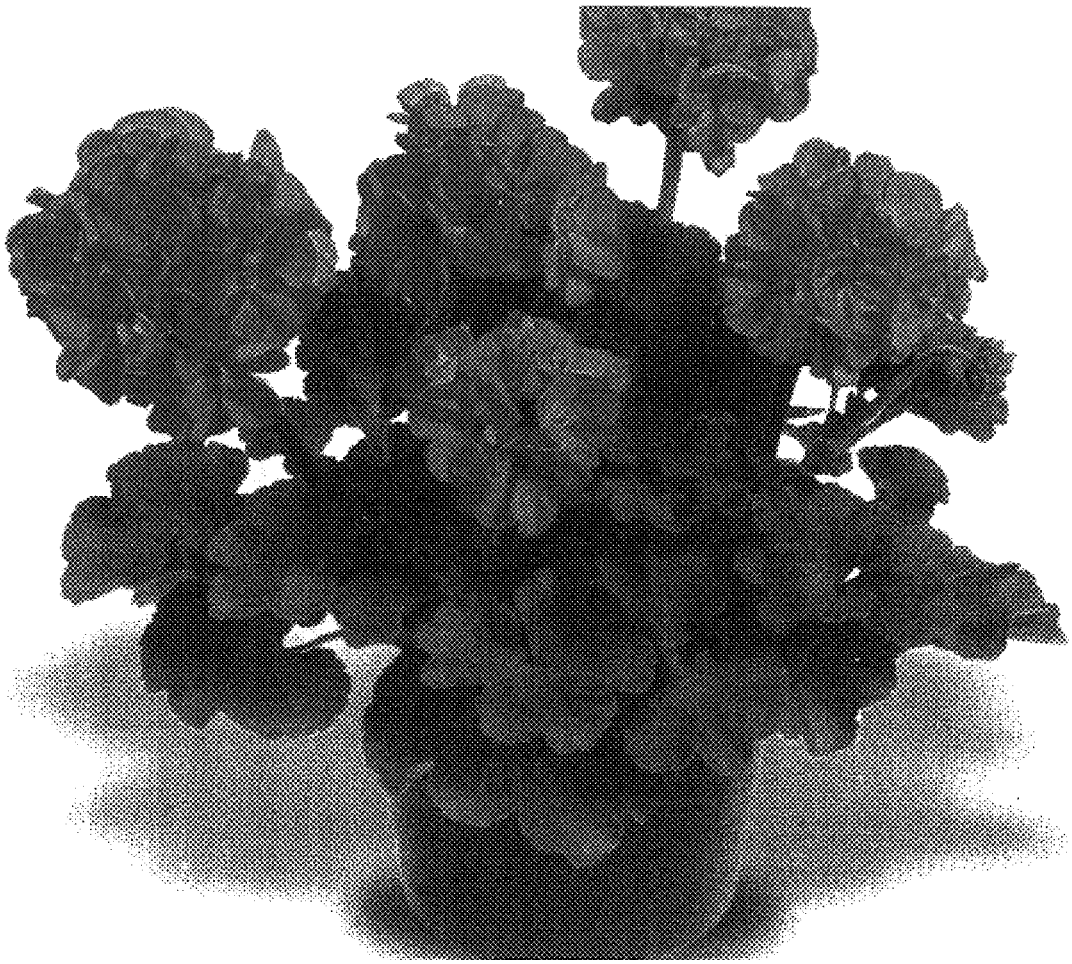

The following detailed description sets forth the characteristics of the new cultivar. The data which defines these characteristics were collected by asexual reproductions carried out in Connellsville, Pa. The color readings were taken indoors under 200–220 foot candles of cool white fluorescent light. The new variety was eight weeks from a rooted cutting when described. Color references are primarily to the 1966 R.H.S. Colour Chart of The Royal Horticultural Society of London.

PLANT

Market class: Zonal.
Time to initiate roots: Approximately 7–10 days at about 23° C.
Time to develop roots: Approximately 21 days at about 23° C.
Time to produce a finished flowering plant from a rooted cutting: About 6–7 weeks in a 10 cm. container.
Rooting habit: Good, normal.
Form: Round-mounded.
Height from media surface to top foliage: 13.0–17.0 cm.
Height from media surface to top of flowers: 28.0–29.5 cm.
Plant diameter: 25.5–29.0 cm.
Vigor: 3 on a scale of 5.
Strength: No artificial support is needed.
Branching habit: Free branching.
Stem:
- *Main stem length.*—11.5–14.0 cm.
- *Diameter.*—0.75–1.0 cm.
- *Color.*—Yellow-Green Group 144A.
- *Texture.*—Leathery texture.
- *Pubescence.*—Present.
- *Internode length.*—1.8–3.7 cm.

Lateral branches:
- *Length.*—Primary: 4.0–8.2 cm. Secondary: Plant is too young to measure.
- *Diameter.*—Primary: 0.7–0.9 cm. Secondary: Plant to too young to measure. Internode length: 1.6–2.2 cm. Texture: Leathery. Pubescence: Present. Color: Yellow-Green Group 144A.

Foliage:
*Arrangement.*—Alternate.
*Stipules.*—Size: 1.0 cm. high by 0.7 cm. wide. Color: Yellow-Green Group 144A.
*Zone.*—None present.
*Size of leaf.*—Length: 8.0–10.5 cm. Width: 5.5–8.1 cm.
*Shape of leaf (generally).*—Reniform with a stalked base.
*Shape of apex.*—Rounded in accordance with reniform leaf shape.
*Shape of base.*—Cordate.
*Texture.*—Velvety.
*Aspect.*—Leaves have a very slight slope increasing from point of connection toward the margin.
*Margin type.*—Crenate.
*Pubescence.*—Upper surface: Moderate. Lower surface: Moderate.
*Color.*—Young leaves: Upper surface: Green Group 137A. Lower surface: Green Group 137C. Mature leaves: Upper surface: Green Group 137A. Lower surface: Green Group 137C.
*Petiole.*—Length: 6.4-13.6 cm. Diameter: 0.25–0.35 cm. Color: Yellow-Green Group 144A.
*Veins.*—Venation type: Palmate. Color: Upper surface: Green Group 137C. Lower surface: Yellow-Green Group 144A.

INFLORESCENCE

Bud: Stage of development when bud characteristics determined: Bud shows color at side but sepals are not parting at the tips.
*Shape of cluster.*—Elliptical.
*Diameter of cluster.*—3.0–3.3 cm.
*Number of buds per cluster.*—23–26.
*Shape of individual bud.*—Ellipse.
*Length of individual bud.*—0.7–0.9 cm.
*Width of individual bud.*—0.5–0.7 cm.
Natural flowering season at specified location(s): Year round horticultural greenhouse crop.
Blooming habit: Continuous and free flowering.
Umbel diameter: 7.0–8.4 cm.
Umbel depth: 5.0–5.5 cm.
Borne: Umbel, flowers on pedicel, pedicel on peduncle.
Inflorescence position: Above foliage.
Number of inflorescences per lateral branch: 1–2.
Lastingness of an individual flower: 10–14 days.
Florets:
*Form.*—Flat and slightly cupped. As flowers mature, the florets gradually become more open/flat.
*Number per umbel.*—15–24.
*Diameter.*—3.5–4.8 cm.
*Depth.*—1.7–2.5 cm.
Petals:
*Color.*—The top two petals of the floret have a white eye whereas the bottom petals do not. Upper surface: The top two or three petals are Red-Purple Group 67B until the bottom third where it fades to White Group 155D. The venation is Red-Purple Group 64B. The point of connection then immediately fades to White Group 155D. The entire bottom petals are Red-Purple Group 67B except for the bottom ¼ of the petal, which slowly fades to White Group 155D. The venation is Red-Purple Group 74B. Lower surface: All petals have a Red-Purple Group 67C margin that fades to Red-Purple Group 73C and finally to White Group 155D as it approaches the base of the petal. The venation is Red-Purple Group 67B with the top two or three petals having heavier venation than the bottom.
*Shape.*—Inverted teardrop.
*Length.*—2.4–2.8 cm.
*Width.*—1.9–2.4 cm.
*Apex shape.*—Smooth and rounded.
*Base shape.*—Tapered to a point.
*Margin.*—Entire; smooth.
*Number per floret.*—6–10.
*Texture.*—Smooth.
*Tonality from a distance.*—Vibrant hot pink flowers with white eyes atop of mounding medium green foliage.
Petaloids:
*Quantity.*—0–2 per floret.
*Shape.*—Splits in a two-pronged unit or are tubular.
*Color (upper and lower surface).*—The upper surface of the petaloids are Red-Purple 67C and fade to White Group 155D at the base. On the lower surface, the petaloids are Red-Purple Group 68B and fade to White Group 155D at the base.
*Length.*—0.7–1.5 cm.
*Width.*—0.3–1.0 cm.
Pedicel:
*Length.*—2.2–2.8 cm.
*Diameter.*—0.13–0.15 cm.
*Color.*—Greyed-Purple Group 185A where the pedicel connects to the floret and fades to Yellow-Green Group 144A as the pedicel approaches the point where it connects to the peduncle.
Peduncle:
*Length.*—14.6–21.9 cm.
*Diameter.*—0.35–0.55 cm.
*Texture.*—A slightly rough leather texture with a slight to moderate amount of pubescence.
*Color.*—Yellow-Green Group 144A.
Sepal:
*Number.*—5.
*Pubescence.*—Moderate.
*Shape.*—Lanceolate.
*Width.*—0.25–0.45 cm.
*Length.*—0.9–1.1 cm.
Fragrance: No unusual fragrance.
Disease resistance: None observed.
Temperature tolerance: None observed.
Drought tolerance: None observed.

REPRODUCTIVE ORGANS

Stamens:
*Number (per flower).*—8–11.
*Filament.*—Length: 0.5–0.7 cm. Color: White Group 155D with the tip being Red-Purple Group 67B.
*Anthers.*—Shape: Oval-like with a slight curve. Length: 0.15–0.8 cm. Color: Greyed-Purple Group 184C.
*Pollen.*—Color: Greyed-Orange Group 169A. Amount: Plentiful.
Pistils:
*Number.*—1.
*Length.*—0.7 cm.
*Style.*—Length: 0.2 cm. Color: Red Group 53B.
*Stigma.*—Shape: Style splits and radiates into 5 parts. Color: Red Group 53B. Size: 0.15 cm. high.
*Ovaries.*—Position: Superior. Pubescence: Present. Length: 0.35 cm. Width: 0.17–0.2 cm. Color: Yellow-Green Group 144A.

I claim:

1. A new and distinct variety of *geranium* plant named 'Patriot Rose Pink' as described and illustrated.

* * * * *